(12) United States Patent
Fine et al.

(10) Patent No.: US 8,389,015 B2
(45) Date of Patent: *Mar. 5, 2013

(54) SALIVARY BIOASSAY FOR EARLY DETECTION OF BONE LOSS

(75) Inventors: Daniel H. Fine, New York, NY (US); David Furgang, East Brunswick, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 227 days.

This patent is subject to a terminal disclaimer.

(21) Appl. No.: 12/724,272

(22) Filed: Mar. 15, 2010

(65) Prior Publication Data
US 2010/0255519 A1    Oct. 7, 2010

Related U.S. Application Data

(63) Continuation-in-part of application No. PCT/US2008/076433, filed on Sep. 15, 2008.

(60) Provisional application No. 60/993,761, filed on Sep. 14, 2007.

(51) Int. Cl.
*A61K 35/12* (2006.01)
(52) U.S. Cl. ........................ 424/520; 424/537
(58) Field of Classification Search .................. 424/520, 424/537
See application file for complete search history.

(56) References Cited

U.S. PATENT DOCUMENTS
2007/0003947 A1   1/2007   DeCarlo
2007/0054281 A1   3/2007   Liew

FOREIGN PATENT DOCUMENTS
WO   2009036447   3/2009

OTHER PUBLICATIONS

Fairney et al. "Studies on the measurement of 25-hydroxy vitamin D in human saliva", British J of Nutrition, 1987, 57:13-25.*
Killi et al. "Collagenase-2 (MMP-8) and collagenase-3 (MMP-13) in adult periodontitis: molecular forms and levels in gingival crevicular fluid and immunolocalisation in gingival tissue", J Clin Periodontol, 2002, 29:224-232.*
dental radiography definition: 1 page, 2011.*
International Search Report for and Written Opinion of the International Searching Authority for International Patent Application No. PCT/US2011/28496 issued Oct. 27, 2011.
Miller, et al. "Current Developments in Salivary Diagnostics," Biomarkers in Medicine, vol. 4 No. 1, Feb. 2010, pp. 177-189.
Garlet, et al., "The Dual Role of p55 Tumor Necrosis Factor-A Receptor in Actinobacillus Actinomycetemcomitans-Induced Experimental Periodontitis: Host Protection and Tissue Destruction", Clin Exp Immunol., Jan. 2007, v. 147 (1), pp. 128-138.
Emingil, et al., "Gingival Crevicular Fluid EMAP-II, MIP-1a and MIP-1b Levels of Patients with Periodontal Disease", J Clin Periodontol, 2005, v. 32, pp. 880-885.
Rhodus, et al., "A Comparison of the Pro-Inflammatory, NF-nB-Dependent Cytokines: TNF-alpha, IL-1-alpha, IL-6 and IL-8 in Different Oral Fluids from Oral Lichen Planus Patients", Clin Immunol., 2005, v. 144, pp. 278-283.
Written Opinion and International Search Report for International Patent Application No. PCT/US08/76433 issued Dec. 2, 2008.

* cited by examiner

*Primary Examiner* — Susan Hanley
*Assistant Examiner* — Bin Shen
(74) *Attorney, Agent, or Firm* — Lowenstein Sandler LLP (57) ABSTRACT

The present invention is directed to methods to detect and diagnose osteoporosis and periodontal disease using salivary biomarkers.

16 Claims, 2 Drawing Sheets

SALIVARY BIOASSAY FOR EARLY DETECTION OF BONE LOSS

This application is a continuation-in-part of International Patent Application No. PCT/US2008/076433, filed Sep. 15, 2008, which claims priority to U.S. Provisional Application Ser. No. 60/993,761, filed Sep. 14, 2007, the disclosures of which are hereby incorporated by reference in their entirety.

FIELD OF THE INVENTION

This invention relates to a method to detect and diagnose osteoporosis and periodontal disease before bone destruction and tooth loss has occurred.

BACKGROUND OF THE INVENTION

Osteoporosis

The World Health Organization ranks osteoporosis just below cardiovascular disease as a public health concern. Recent statistics indicate that approximately 75 million Americans, Europeans and Japanese are affected by osteoporosis, including one third of women 60-70 and two thirds of women in their 80's or above. Twenty-one million women have been diagnosed with osteopenia (low bone mass) while about eight million American women have osteoporosis. Over one million fractures are attributed to individuals with osteoporosis.

Conventional radiographs are not sensitive enough to detect osteoporosis until bone density mineral has been reduced by over 50%. Dual-energy x-ray absorptiometry (DXA) and quantitative computed tomography are the most widely used methods for detecting osteoporosis. The cytokines responsible for bone loss include RANKL (receptor activated nuclear Kappa ligand) and osteoprotegerin as well as agents such as MIP 1a (macrophage inflammatory protein alpha) and alkaline phosphatase. In essence some of the same markers that relate to bone loss in periodontal disease are associated with bone loss in osteoporosis. Laboratory tests used to diagnose osteoporosis have relied on markers that include osteocalcin and bone alkaline phosphatase. These markers are detected in blood samples and are not currently used as diagnostic tests.

Osteoporosis is seen as a "silent" risk factor for bone fracture. Bone mineral density testing is recommended for all post menopausal women younger than 65 who have one additional risk factor for osteoporosis beyond menopause.

Periodontal Disease

Periodontal disease is another disease whose end point is bone loss. Periodontal disease is an inflammatory disease that begins as an inflammation of the gingival soft tissues (gums) and then proceeds to affect the supporting structures of the tooth in its boney socket. At present periodontal disease is the most pressing dental malady that if untreated can result in tooth loss. Further, recent evidence suggests that this chronic dental infection that results in widespread oral inflammation can contribute to an increased risk for systemic complications including an increased risk for heart disease. With the discovery of fluoride and the resulting reduction in the prevalence of caries, periodontal disease and its earliest manifestation gingivitis has become the most prevalent and costly of dental infections. Gingivitis and its sequelae, periodontal disease affects over 50% of the adult population.

Oral bacteria form a plaque biofilm that can initiate gingival inflammation. Under the appropriate circumstances gingivitis can lead to periodontitis which is manifested as an inflammatory induced destruction of the honey support of the teeth. The disease is pandemic, costly, can result in tooth loss, and is also conjectured to increase the risk for coronary heart disease and other systemic conditions.

Currently the existing technology used by a dentist or dental health professional to detect periodontal disease relies on a clinical examination that includes a periodontal probe and/or an x-ray. It is well known that these methods are imperfect because they are operator sensitive, time consuming and detect past history of tissue destruction. Thus there remains a need for improved ways of detecting periodontal disease.

Bone loss, the ultimate proof of disease, is measured by radiograph and is an end stage of disease, which for the most part is irreversible. The periodontal complex is best described as a peg in a socket, the tooth represented by the peg and the alveolus, or surrounding bone, represented by the socket. The tooth is connected to its socket by fibers made of collagen that enable the tooth to respond to the forces of mastication and clenching and grinding. Inflammation causes bone loss which occurs by virtue of osteoclasts (bone eating cells) which eat away the bone, widen the socket, leading the affected tooth to become loose and ultimately non-functional. Bone loss of the periodontal tissues takes anywhere from 6-18 months to manifest itself.

Longitudinal models of infectious diseases are capable of providing insights into tissue destructive events provoked by infectious agents. For example Agace et al. have documented the initial inflammatory response in humans to *Escherichia coli* that provoke urinary tract infections. Most studies of pathogenesis have been relegated to animal models of disease which while useful have their own limitations. Very few prospective studies of human periodontal disease have been undertaken. Over the past several years our group, and others, (Bueno et al 1999) have been working on a longitudinal model of a particular form of periodontal disease found in children called localized aggressive periodontitis (LAP). As a longitudinal model of periodontal disease, LAP has several advantages. First, since periodontal disease is unusual in children and because of a distinctive molar/incisor pattern of distribution, LAP is relatively simple to diagnose. Second, there is convincing evidence that a particular microbe, *Aggregatibacter actinomycetemcomitans* infects those children who have LAP. Moreover, since the disease progresses rapidly, breakdown can occur between 1-3 years. Thus, it is possible to study LAP over a relatively short period of time as compared to chronic adult periodontitis which advances slowly over an undetermined time period. Recently two longitudinal studies have been done utilizing populations at risk for LAP. Both studies have shown that *A. actinomycetemcomitans* carriers are at risk; but neither reported on host factors related to LAP onset.

Diagnosis of periodontal disease is initially based on measurements of soft tissue detachment from the tooth, which results in a periodontal pocket. Methods used to probe for attachment loss and to detect bone loss, the hallmark of the irreversible stage of periodontal disease, while quite specific are not very sensitive, and often delay diagnosis. A number of scientific advances have spawned technologies that are capable of detecting nanograms or picograms levels of inflammatory markers in bodily fluids. These technologies could potentially be used to develop into tests for early clinical diagnosis, which if successful could provide earlier warning of disease onset as compared to the relatively insensitive methods used currently. However, to date many of the candidate biomarkers that have been tested have not been able to distinguish between forms of gingivitis that are reversible, and periodontitis that is irreversible. New biomarkers are required but cannot be developed in the absence of a longitudinal model of disease.

OBJECTS AND SUMMARY OF THE INVENTION

It is an object of the present invention to provide a method for the early detection of osteoporosis and bone loss in periodontal disease.

It is an object of certain embodiments of the present invention to provide a biomarker for use in the early detection of osteoporosis and bone loss in periodontal disease.

It is an object of certain embodiments of the present invention to provide a method for use in the early detection of osteoporosis and bone loss in periodontal disease that can be used by medical practitioners, including dental practitioners.

It is an object of certain embodiments of the present invention to provide a method for use in the early detection of osteoporosis and bone loss in periodontal disease that can be used by patients.

It is an object of certain embodiments of the present invention to provide a kit that can be utilized by medical practitioners, including dental practitioners, for the early detection of osteoporosis and bone loss in periodontal disease.

It is an object of certain embodiments of the present invention to provide a kit that can be utilized by patients for the early detection of osteoporosis and bone loss in periodontal disease.

It is an object of certain embodiments of the present invention to provide a biomarker for use in the early detection of osteoporosis and bone loss in periodontal disease.

It is an object of certain embodiments of the present invention to provide an indicator of bone resorption while teeth are being moved in orthodontic tooth movement.

It is an object of certain embodiments of the present invention to provide a method that can be used to titer bone resorption in implant dentistry.

It is an object of certain embodiments of the present invention to provide a method that can be used to titer bone resorption in osteoporosis prior to visualization by x-ray.

The term "indicates early-stage periodontal bone loss" means that the patient has early-stage periodontal bone loss or has the potential to develop periodontal bone loss.

BRIEF DESCRIPTION OF THE DRAWINGS

Figure IA is a graphical depiction of the measured level of MIP 1α as compared to Aa type.

DETAILED DESCRIPTION

The present invention in certain embodiments is directed to a method of detecting early-stage osteoporosis and/or periodontal bone loss in a patient comprising identifying one or more biomarkers in a bodily fluid of a patient at a level that indicates early-stage osteoporosis and/or periodontal bone loss.

Periodontal Disease

Preferably, the biomarker is a cytokine and most preferably the cytokine is MIP1α, a chemokine that initiates conversion of pleuripotential cells to differentiate into osteoclasts. The MIP 1α can be detected in patients prior to bone loss and thus acts as an early indicator of the onset of disease. This invention allows a practitioner (or as suggested a patient at home using a home test) to use, e.g., saliva, to assess the earliest stages of periodontal bone loss so that a vulnerable patient can be identified. This test allows such a patient to seek treatment that can prevent further loss and thus save his or her teeth. Further once the patient has been identified then the dentist can, using a modification of the test, pinpoint the tooth or teeth in the patient's mouth that require treatment so that treatment could be limited to those teeth in the patients mouth that require intervention.

In embodiments directed to the presence of MIP 1α in saliva, the level that is used as an indicator of to indicate early-stage periodontal bone loss can be, e.g., greater than about 200 pg/ml, greater than about 400 pg/ml, greater than about 600 pg/ml, or greater than about 800 pg/ml.

In other embodiments the presence of MIP 1α in saliva is detected at a level from about 200 pg/ml to about 2000 pg/ml, from about 500 pg/ml to about 1,500 pg/ml, or from about 750 pg/ml to about 1,250 pg/ml to indicate early-stage periodontal bone loss.

In preferred embodiments, the biomarker is identified prior to radiographic evidence of bone loss. This allows the early intervention to prevent or minimize progression of the disease and also prevents or minimizes the exposure of the patient to radiation.

The present invention also is directed to a kit for detecting early-stage periodontal bone loss comprising a reagent that indicates the presence of a biomarker in a bodily fluid of a patient at a level that indicates early-stage periodontal bone loss and a device for contacting the bodily fluid with the biomarker.

The kit optionally includes instructions that explain that the presence of the biomarker at the level indicates early-stage periodontal bone loss.

In certain embodiments the device includes an apparatus for mixing the reagent with the bodily fluid. In another embodiment, the reagent can be on a strip that is contacted with saliva by placing the strip on the tongue of the patient.

In a particular embodiment, the method or kit utilizes Luminex xMAP technology to detect the biomarker. In one embodiment, a salivary sample is placed into plate prepared with internally labeled fluorophore beads. The mixture of sample and beads is agitated and incubated. Labeled dyes contained within the beads are excited, exposed to a washing strategy, and then subjected to detection of activated fluorphores.

In certain embodiments, the biomarkers used to detect early-stage periodontal bone loss include, but are not limited to, Osteocalcin, RANK L and soluble RANKL, Osteoprotegrin, MIP 1 alpha and Alkaline phosphatase. Additionally, the biomarkers described below with respect to early detection of osteoporosis may also be used.

Other embodiments of the invention are directed to a method of detecting increased periodontal pocket depth in a patient comprising identifying a biomarker in a bodily fluid of a patient wherein the level of the biomarker directly correlate with the pocket depth and corresponding kits.

In other applications of the present invention, a dental practitioner can titrate pressure being exerted on teeth so that pressure to move teeth can be increased or decreased to allow for more or less bone resorption (titrate pressure vs. movement) and corresponding tooth movement that accompanies this pressure.

Osteoporosis

Still other applications of the present invention include the tittering of bone resorption in implant dentistry and the tittering of bone resorption in osteoporosis prior to visualization with radiography.

In embodiments directed to the presence of MIP 1α in saliva, the level that is used as an indicator of to indicate osteoporosis can be, e.g., greater than about 200 pg/ml, greater than about 400 pg/ml, greater than about 600 pg/ml, or greater than about 800 pg/ml.

In other embodiments the presence of MIP 1α in saliva is detected at a level from about 200 pg/ml to about 2000 pg/ml, from about 500 pg/ml to about 1,500 pg/ml, or from about 750 pg/ml to about 1,250 pg/ml to indicate osteoporosis.

In preferred embodiments, the biomarker is identified prior to radiographic evidence of osteoporosis. This allows the early intervention to prevent or minimize progression of the disease and also prevents or minimizes the exposure of the patient to radiation.

The present invention also is directed to a kit for detecting osteoporosis comprising a reagent that indicates the presence of a biomarker in a bodily fluid of a patient at a level that indicates osteoporosis loss and a device for contacting the bodily fluid with the biomarker.

The kit optionally includes instructions that explain that the presence of the biomarker at the level indicates osteoporosis.

In certain embodiments the device includes an apparatus for mixing the reagent with the bodily fluid. In another embodiment, the reagent can be on a strip that is contacted with saliva by placing the strip on the tongue of the patient.

In a particular embodiment, the method or kit utilizes Luminex xMAP technology to detect the biomarker. In one embodiment, a salivary sample is placed into plate prepared with internally labeled fluorophore beads. The mixture of sample and beads is agitated and incubated. Labeled dyes contained within the beads are excited, exposed to a washing strategy, and then subjected to detection of activated fluorphores.

Other embodiments of the invention are directed to a method of detecting increased periodontal pocket depth in a patient comprising identifying a biomarker in a bodily fluid of a patient wherein the level of the biomarker directly correlate with the pocket depth and corresponding kits.

In addition to the biomarkers used to detect periodontal disease, the following biomarkers may be used for the study of osteoporosis: 1.25 Dihyroxy Vitamin D, 25-Hydroxy Vitamin D, TRAP 5b (tartrate resistant acid phosphatase—5b) TRACP 5b, Deoxypyridinoline, Fibroblast growth factor-23 (FGF-23), Intact parathyroid hormone (PTH), Matrix metalloproteinase-8 and 13 (MMP 8 and MMP 13), C-terminal telopeptides of Type 1 collagen (alpha CTX-I).

Initially efforts will be made to correlate levels of bone markers with the patients current osteoporosis status. It is hypothesized that the biomarkers used to detect early-stage periodontal disease may be different from those which detect osteoporosis.

To start, levels of osteocalcin, alkaline phosphatase, RANKL, Osteoprotegerin and MIP 1a in the saliva of postmenopausal women in relationship to their DXA status will be assessed. Thus a subject with a T score of >−1.0 is considered normal, while a subject with a score of −2.5 to −1.0 is considered osteopenic while a subject with a T score of −2.5 is considered to be osteoporotic. Since the Z-score is age related we will also compare salivary levels of biomarkers to the Z-score as well. At this time although bio markers for osteoporosis are available in serum or blood samples there has not been a serious effort to use these markers to assist in the diagnosis of this condition. The present invention would allow a practitioner (or as suggested a patient at home using a home test) to use saliva to assess the earliest stages of bone loss so that a vulnerable patient can be identified. This test would allow such a patient to seek treatment that can prevent further loss. Further once the patient has been identified then, using a modification of the test, treatment could be tittered to those patients that require intervention.

EXAMPLES

Example 1

Periodontal Disease

This study details the survey of cytokines/chemokines obtained from saliva of at risk subjects who were enrolled in a longitudinal cohort study of a specialized form of periodontal disease that occurs in adolescents, localized aggressive periodontitis (LAP).

The study involves the association of *Aggregatibacter actinomycetemcomitans* (Aa) with the initiation of LAP. This disease has afforded us the opportunity to study bone loss because, 1) the disease occurs in juveniles (this is a rare event and thus makes the disease easier to identify when it happens because it is so rare in children), 2) the disease is localized to first molars and therefore we can focus on first molars (there are four; as opposed to the 28 other teeth which we would have to follow if we studied adults), 3) it is rapidly progressive (and occurs in one to three years as opposed to disease in adults which has no well defined time limit) and 4) is associated with a particular microbe (Aa; as opposed to adult disease which has an ill defined provoking microflora).

Saliva from subjects who were healthy and *A. actinomycetemcomitans* positive at screening and who developed bone loss, were compared to subjects who were *A. actimycetein-comitans*-positive and *A. actinomycetemcomitans*-negative who remained healthy. The goal of this study was to determine whether salivary biomarkers that were indicative of the initial stages of inflammatory periodontitis and bone loss could be detected prior to radiographic evidence of bone loss in a group of LAP susceptible subjects. This example documents the elevation of MIP1α, a chemokine that recruits osteoclast progenitors, in the saliva of students who developed bone loss. Results from the example suggest that MIP 1a could serve as a biomarker of early events in inflammatory induced periodontal bone loss that precedes radiographic evidence.

Materials and Methods

A calibration exercise was conducted for measurement of periodontal pocketing, attachment loss and radiographic detection of bone loss. Results of the calibration exercise demonstrated 80% inter-examiner agreement and 90% intra-examiner repeatability. A detailed description of the procedures has been reported.

At the screening visit each student was sampled and examined for oral soft tissue lesions, caries and periodontal disease. For the periodontal examination, standard probing measurements were done on six surfaces on each tooth. Any site ≧4 mm was re-examined for attachment level measurements. Potential disease was defined as any pocket ≧6 mm with associated attachment loss ≧2 mm. Students in this category were scheduled for recall within a 3-month period or sooner in order to minimize any irreversible consequences of disease. Each student was given a prophylaxis and oral hygiene instruction.

A recall visit was scheduled within 6-months of screening or sooner depending on the students' periodontal status. Recall was identical to screening except for the addition of 2-4 horizontal bitewing radiographs for detection of bone loss.

Most participants were students with a mixed dentition and partially erupted molar teeth which adds to measurement variability (Albandar). As a result of this potential source of measurement error we chose to use radiographs as the main determinant of periodontal disease. Disease was defined as crestal loss of lamina dura and interproximal alveolar bone resorption in the region of one or more molars or incisors as visualized by radiography. Pocket depths and attachment levels were also recorded but in the initial analysis evidence of bone loss was required since our goal was to relate the presence of specific cytokines to bone loss. As mentioned, to prevent any serious consequences relating to the aggressive loss of bone, subjects with potential disease were re-scheduled for re-probing and attachment level measurements as well as radiographic evaluation within a 3-month period following screening. On evidence of bone loss the student was referred for treatment provided at no cost in the University practice facility. If radiographs did not show bone loss, students were returned to the 6-month recall schedule.

At each visit the following samples were collected: unstimulated saliva, buccal epithelial cells [BEC], and subgingival plaque from pockets $\geq 5$ mm. Saliva was used to assess inflammatory cytokines. BEC and subgingival plaque samples were used to determine the presence or absence of $A.$ $actinomycetemcomitans$. For saliva collection, students expectorated into a 50 ml wide-mouthed polystyrene tube placed over ice. Five ml of saliva was collected and then subjected to centrifugation at 10,000×g for 30 min. The supernatant was decanted and the clarified saliva was stored at $-80°$ C. SEC samples were obtained by gently scraping the surface of the buccal mucosa with a wooden tongue depressor. Cells were collected in a 50 ml Pyrex tube containing 2 ml of phosphate buffered saline (PBS). BECs were subjected to vortex agitation for 15 seconds after which 100 ul was removed for plating on AAGM agar. The remaining reservoir of epithelial cells was stored at $-80°$ C. Pocket samples were taken for any subgingival pocket >5 mm by placing two sterile endodontic paper points in the pocket site for 10 sec. All sites sampled in a given subject were pooled in 2 ml of PBS, subjected to vortex agitation for 15 sec, after which 100 ul was removed for plating on AAGM agar for isolation of $A.$ $actinomycetemcomitans$.

One thousand and forty-five students ages 11-17 were screened for periodontal disease and sampled for $A.$ $actinomycetemcomitans$. 147 of these students were shown to harbor $A.$ $actinomycetemcomitans$ (Aa-positive). A longitudinal study was designed to follow Aa-positive and matched Aa-negative students at 6-month intervals for 2-3 years. Thus-far 37 Aa-positive and 58 Aa-negative students have been followed for $\geq 1$ yr and 7 of these 36 who were healthy at screening have developed bone loss. One of the 37 students had bone loss at screening, while none of the 58 Aa-negative students have shown bone loss at any visit. Initially, cytokines were assessed in the saliva of 7 Aa-positive students who developed bone loss 6-12 mo prior to bone loss. These samples were compared to samples obtained from 7 Aa-positive and 7 Aa-negative students who remained healthy and were matched for sex, age and race to the 7 students who developed bone loss. Following evaluation of these 21 students, 13 Aa-negative and 13 Aa-positive students were added for analysis as was one Aa-positive student who had bone loss at screening. This study reports on cytokine levels from the stored saliva obtained from these 48 students.

Microbiological and Cytokine Procedures

For identification of $A.$ $actinomycetemcomitans$ positive students, 100-ul aliquots of BECs and/or pocket samples were plated on AAGM agar and grown for 3-4 days in an incubator at 37° C. in 10% $CO_2$. $A.$ $actinomycetemcomitans$ was identified by biochemical testing and by the polymerase chain reaction [PCR].

$actinomycetemcomitans$-negative students were identified as follows. Stored BEC and/or pockets samples were subjected to DNA extraction and evaluation of $A.$ $actinomycetemcomitans$ DNA by PCR. DNA was extracted using the Qiagen DNeasy Kit [Qiagen Inc., Valencia, Calif., Cat #69504] Gram-Negative Bacteria Protocol. This procedure was repeated 2×'s to confirm that the student was $A.$ $actinomycetemcomitans$-negative.

The presence and level of 21 cytokines in saliva was determined by the Luminex xMAP technology. 100 ul salivary sample was placed into a 96-well plate prepared with internally labeled fluorophore beads. The mixture of sample and beads was agitated and incubated for 2 hrs at RT. Labeled dyes contained within the beads were excited by laser, exposed to a washing strategy, and then subjected to detection of activated fluorphores. All tests are run simultaneously to assure standardization. The limit of detection was between 1-500 pg.

Statistical Analysis

The three groups ($A.$ $actinomycetemcomitans$-positive with bone loss, $A.$ $actinomycetemcomitans$-positive healthy and $A.$ $actinomycetemcomitans$-negative healthy) were compared. The statistical difference between groups for each of the 21 cytokine/chemokine was analyzed by ANOVA. Differences were considered significant if they achieved a p value of $\leq 0.05$.

Similar statistical comparisons were made for $A.$ $actinomycetemcomitans$-positive students to determine whether recovery from buccal sites differed from pocket sites. Tukey's Honest Statistical Difference (HSD) test was performed to elucidate the relationship between pairs of comparison within the ANOVA.

In addition, a bivariate linear regression analysis was used to evaluate cytokine levels vs. pocket depth or maximum number of pockets per individual. Due to the distribution of the data, Spearman's rank order correlations were used to describe the relationship between the two cytokines and mean pocket depth. The strength of the cytokines and $A.$ $actinomycetemcomitans$ to predict future pocket depth were also compared with ANCOVA (adjusting for age, gender and race). This was done in order to determine which variable was a better candidate for predicting future periodontal destruction as evidenced by the number of 6 mm. pockets. IL 1β and MIP 1α sensitivity and specificity relative to detection of bone loss was determined. Sensitivity was defined as the number of bone loss positive students that were above threshold levels (for MIP 1α or IL 1β) divided by the total number of bone loss positive students. Specificity was defined as the number of bone loss negative students below threshold levels (for MIP 1α or IL 1β) divided by the total number of bone loss negative students.

Results

Table 1 shows the demographic distribution of students evaluated; 26 were female, 20 were African-American and 18 were Hispanic.

TABLE 1

Demographics of Subjects

| Subject Category | Aa-Negative Healthy | Aa-Positive Healthy | Aa-Positive LAP |
|---|---|---|---|
| N | 20 | 20 | 8 |
| Mean Age | 15.1 ± 1.2 | 15.3 ± 1.4 | 15.8 ± 1.0 |
| Males | 8 | 10 | 4 |
| Females | 12 | 10 | 4 |
| African-American | 8 | 10 | 5 |
| Hispanics | 10 | 8 | 3 |
| Caucasian | 1 | 1 | 0 |
| Asian | 1 | 1 | 0 |

Aa = A. actinomycetemcomitans

The students' ages were approximately similar. The initial evaluation of IL 1β and MIP 1α compared 7 students in each of 3 groups as indicated in Table 2.

TABLE 2

Relationship of Cytokine Levels in Saliva to Disease Levels

|  | Aa-Negative Healthy (N = 7) | Aa-Positive Healthy (N = 7) | Aa-Positive LAP (N = 7) |
|---|---|---|---|
| IL-1β | 21.6 ± 19.1 | 13.5 ± 4.3 | 39.2 ± 26.2 |
| MIP-1α | 20.5 ± 6.8 | 28.8 ± 6.8 | 420 ± 42.8* |

Aa—A. actinomycetemcomitans
*= Significantly higher by ANOVA and post-hoc analyses Cytokine/chemokine level reported as pg/ml The following cytokines, IL-2, IL-3, IL-4, IL-5, IL-9, RANTES, VEGF, KC, and TNFα were not detected. The following cytokines, GMCSF, IFNγ, IL-1α, IL-6, IL-8, IL-10, IL-12 (p40), 1L-12 (p70), IL-13, IL-17 were detected but no significant differences were found when the three groups were compared. IL 1β was elevated in the $A.$ $actinomycetemcomitans$-positive breakdown group as compared to the two other groups but differences were not significant (p=0.147; Table 2). However, MIP 1α (pg/ml) was significantly elevated in the $A.$ $actinomycetemcomitans$-positive LAP group 6-9 months prior to detection of bone loss (p ≦0.001; Table 2). While 7 of 7 $A.$ $actinomycetemcomitans$-positive students showed elevated levels of MIP 1α prior to bone loss, only one of the 14 control students showed elevated MIP 1α and the level was half that seen in the students with bone loss.

Figure 1A:
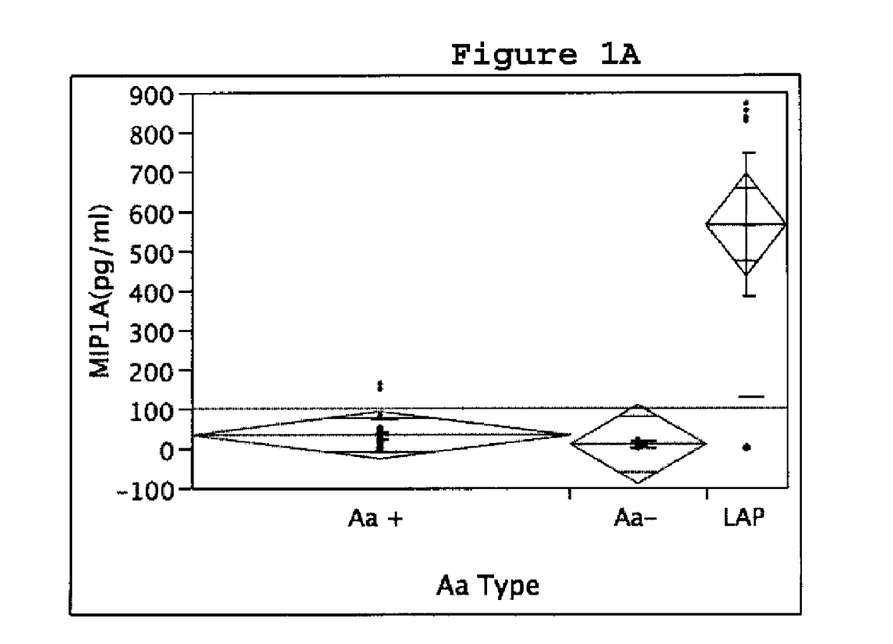
Figure 1B:
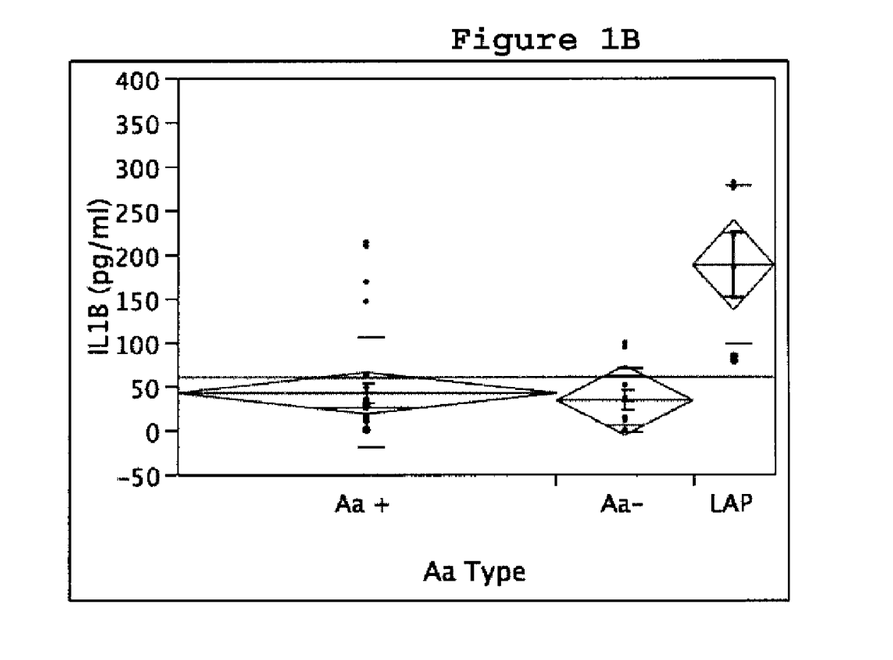
FIG. 1B is a graphical depiction of the measured level of IL β as compared to Aa type.

In an effort to confirm this data we added students in the $A.$ $actinomycetemcomitans$-positive and $A.$ $actinomycetemcomitans$-negative groups who remained healthy to determine if any of these students exceeded the basal levels of MIP 1α or IL 1β seen in the initial analysis. Only one additional student could be added to the bone loss group since only eight students in total showed bone loss. This one student had bone loss at screening. The levels of MIP 1α remained approximately 50 times higher in the group that experienced bone loss as compared to controls (p ≦0.0001; Fig. 1a). When additional healthy students were included, the levels of IL 1β were now statistically significantly elevated in the bone loss group as compared to controls (Fig. 1b).

MIP 1α had a specificity of 96.8% (30=number of bone loss negatives below threshold levels of 100 pg/ml/30+1=total number of bone loss negatives) and a sensitivity of 100% (7=number of bone loss positive above the threshold/7 total number of students with bone loss), while IL 1β had a specificity of 90.3% (28/31) and a sensitivity of 85.7% (6/7) for bone loss.

Figure 2A:
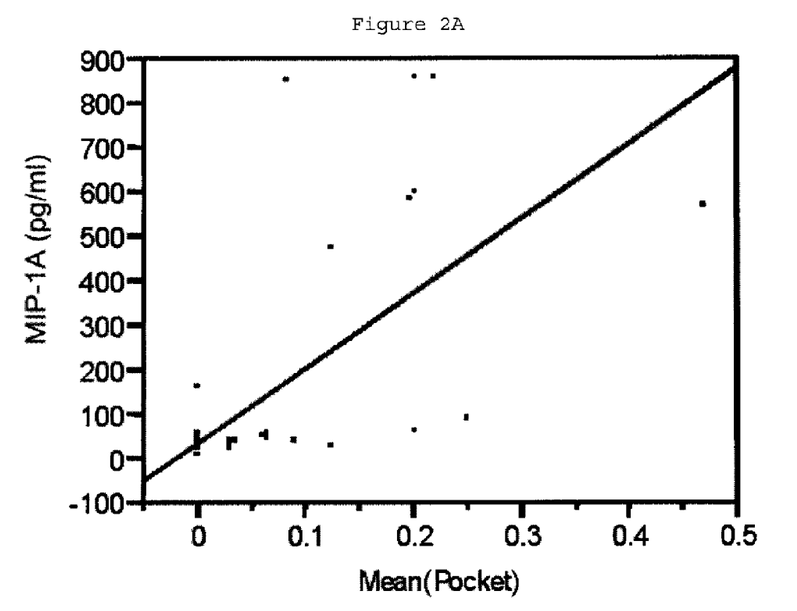
FIG. 2A depicts the relationship between increasing mean pocket depths and increasing levels of MIP 1α.
Figure 2B:
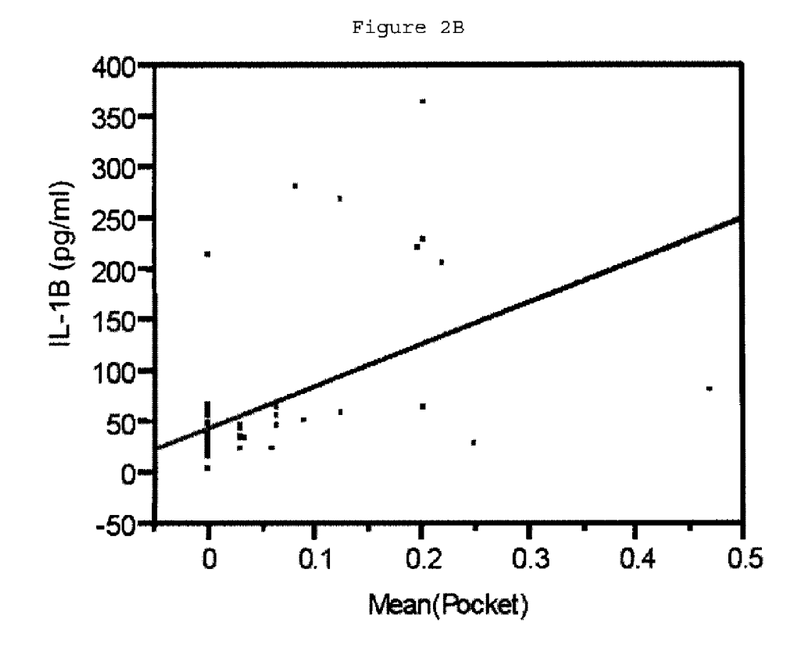
FIG. 2B depicts the relationship between increasing mean pocket depths and increasing levels of IL β.

Since only those students with $A.$ $actinomycetemcomitans$ developed bone loss we compared sites of recovery of $A.$ $actinomycetemcomitans$ to levels of MIP1α and IL 1β in these $A.$ $actinomycetemcomitans$-positive students using a Students t test. No differences were found when cytokine levels in saliva were assessed in students where $A.$ $actinomycetemcomitans$ was recovered from buccal sites as compared to $A.$ $actinomycetemcomitans$ recovered from pocket sites (data not shown). However when pocket depths were evaluated and compared to cytokine levels by linear regression analysis, a direct relationship between increasing mean pocket depths and increasing levels of MIP 1a (r=0.57; p <0.0001) and IL 1b (r=0.56; p <0.0001) was seen (FIGS. 2a, 2b).

Table 3 presents the results of ANCOVA in which the independent variables in the table (time in study, age, gender, race, presence of $A.$ $actinomycetemcomitans$, IL-1β (pg/ml), and MIP-1α (pg/ml) were related to the number of six mm pockets, the dependent variable.

TABLE 3

Analysis of Covariance of all factors as they relate to the number of 6 mm pockets

| Variable | DF | Sum of Squares | Prob > F |
|---|---|---|---|
| Time from sample | 1 | 0.12 | 0.778 |
| Age | 1 | 1.65 | 0.292 |
| Gender | 1 | 0.59 | 0.525 |
| Race | 5 | 0.84 | 0.988 |
| Aa | 1 | 2.39 | 0.206 |
| IL-1β (pg/m1) | 1 | 5.14 | −0.067 |
| MIP-1α (pg/ml) | 1 | 17.59 | 0.001 |

The goal of the analysis was to determine which of three variables ($A.$ $actinomycetemcomitans$, MIP-1α (pg/ml), and IL-1β (3 (pg/ml)) had the strongest relationship with periodontal destruction as measured by the number of six mm. pockets. The sums of squares and the significance levels indicate that the strongest relationship was between MIP-1α (pg/ml) and the sum of 6 mm. pockets (ss. 17.59, p <0.001). It should be noted that if IL-1β (pg/ml), or $A.$ $actinomycetemcomitans$ were the only variable in the model in addition to the demographic covariates, that they were also significantly related to the sum of the six mm pockets (analysis not shown). Thus $A.$ $actinomycetemcomitans$ and IL 1b parallel the elevations seen in MIP 1α. This suggests that the variables are co-linear and that MEP-1α (pg/ml) had the strongest relationship with periodontal destruction as measured by the number of six mm pockets of the three variables assessed (see Table 3).

Discussion

It is proposed that periodontal disease progresses from increased pocket depth to bone loss which marks the decisive and irreversible stage of disease. Cross-sectional studies are limited in their ability to capture time dependant events that would herald the transition from pocket deepening to attachment loss to bone loss. In contrast, longitudinal studies are capable of highlighting these critically important sequential events. A significant literature suggests that radiographs lack the sensitivity required to define the transition from attachment loss to early bone loss and thus depict past history of disease. Radiographic depiction of bone loss relies on detection of a threshold of calcium depletion in bone, which can begin 6-9 months before this event can be visualized. This delayed discovery postpones and complicates treatment. Therefore a biomarker that predates x-ray evidence of bone loss by several months is highly desirable.

Recently, our group performed a longitudinal study in Newark to focus on African-American and Hispanic children who harbored *A. actinomycetemcomitans* and thus were thought to be at risk for LAP. Results indicated that LAP prevalence in African-American and Hispanic children from Newark was similar to data seen in the NHANES study. We were particularly interested in the risk projected for healthy children who harbored *A. actinomycetemcomitans*. Thus a longitudinal study was designed to follow initially healthy *A. actinomycetemcomitans* positive and *A. actinomycetemcomitans*-negative students at 6-9 month intervals. 38 *A. actinomycetemcomitans*-positive healthy children were followed for ≧1 yr and about 18% (7 of 37) developed bone loss while none of the 58 matched *A. actinomycetemcomitans*-negative students developed bone loss. Of all the students followed, 1.8% (7 of the 96) developed LAP, which approximates the LAP national average for African-American and Hispanic children. Thirty of 37 who harbored *A. actinomycetemcomitans* (about 80%) did not show bone loss and remained healthy over the course of the study. A second longitudinal study done in Morocco also indicated that children with *A. actinomycetemcomitans* were at a significant increased risk for LAP. A test discriminating between those *A. actinomycetemcomitans*-positive subjects who develop disease (18%), those *A. actinomycetemcomitans*-positive subjects who may develop disease from those who will remain healthy is warranted.

The data derived from this study is based on a subset of students who overtime went from health to bone loss. Bone loss was used to identify disease because it marked a well-defined step in the disease process that is irreversible and can be separated from inflammatory gingivitis, which is reversible. Thus, conclusions derived from this study are based on a strict definition of periodontal disease that separate groups by one event, namely, bone loss. Students with bone loss showed a 50-fold elevation of MIP 1α, a chemokine that stimulates recruitment of osteoclast progenitors and the formation of osteoclasts. Chemokines are small (8-12 kDa) biologically active proteins, secreted by inflammatory cells. The chemokines form a gradient that attracts specific cells. The result is an advancing front of highly active cells that confront the challenging irritants. MIP 1α is a biologically active chemokine primarily known as a chemotactic agent for monocytes. However, MIP1α also acts to stimulate monocytes and/or osteoclast progenitor cells to become active osteoclasts. In the pathogenesis of multiple myeloma, MIP 1α has been shown to be elevated several months prior to radiographic detection of bone loss. With respect to dental infections, MIP 1α has been shown to be elevated in patients with periapical osseous lesions, and in periodontal disease, although results are not conclusive.

Our secondary analysis showed that IL 1β was also elevated. Several in vivo studies have shown that IL 1β levels in gingival crevice fluid are elevated in sites that show alveolar bone loss in patients with active periodontal disease. Most recently it was shown that *A. actinomycetemcomitans* and *Porphyromonas gingivalis* LPS induced MIP 1α expression in PMNs and gingival epithelial cells. Further, it was shown that *A. actinomycetemcomitans* and *P. gingivalis* LPS and IL 1β can stimulate these progenitor cells to activate osteoclasts.

The findings from the current study were considered highly informative for the following reasons. Of 21 cytokines assessed only one, MIP 1α, was significantly elevated in the saliva in our initial assay. The fact that MIP 1α has been shown to have a powerful biological link to bone loss in other bone resorbing diseases adds credibility to its use as a biomarker for identification of a patient at risk for bone loss in periodontal disease. It is also of interest that the second cytokine, IL 1β, was significantly elevated in our subsequent analysis. IL 1β is a cytokine that can stimulate cells to produce MIP 1α as well as RANK another important precursor of bone loss.

Only one interproximal area of bone loss was sufficient for detection of elevated MIP 1α or IL 1β in saliva. Since evidence of bone loss was absent 6-9 months prior to radiographic evidence and since it was mandated that students be exited from the study as soon as one site with bone loss was detected, it is most likely that these cytokines were derived from a single gingival crevice site overlying the one tooth that ultimately developed bone loss.

Increasing levels of MIP 1α correlated with increasing pocket depth but not with the number of pockets that developed. Levels of IL 1b also increased in a similar manner. Since periodontal disease is thought to progress from increasing pocket depth to attachment loss to bone loss MIP 1α and IL 1β may be signals of developing disease. While IL 1β was elevated in this study and appears to correlate with levels of MIP 1α, IL 1β is a cytokine that is elevated in both gingival and periodontal inflammation. Thus IL-1β cannot be viewed as a specific marker of bone loss. Furthermore, IL 1β levels showed only a five-fold difference and thus may not be as capable of discriminating between health and disease.

The approximately 50-fold increase above basal levels of MIP 1α in subjects prior to bone loss provides us with a reasonable level of confidence that salivary MIP 1α levels can be used as an early indication of bone loss. Moreover, ANCOVA modeling indicated that MIP 1α was the dominant independent variable examined in relation to the number of pockets six mm or greater. Using this statistical modeling method IL 1β and *A. actinomycetemcomitans* were not as strongly related to the number of pockets.

In conclusion, the longitudinal design used in this study has provided us with data to suggest that salivary levels of the chemokine MIP 1α may be used as a biomarker for identification of a patient in advance of radiographic evidence of bone loss. This evidence is compelling since it is based on samples obtained a minimum of 6-9 months prior to radiographic detection of bone loss in a group of LAP subjects. In conjunction with previous findings, it may be possible to translate this data into a two-step screen for subjects susceptible to bone loss in LAP; the first screen for detection of those who carry *A. actinomycetemcomitans*, and a second screen utilizing MIP 1α to discriminate between the *A. actinomycetemcomitans* carriers who will develop bone loss as opposed to those who remain healthy. Moreover, such a test can pave the way for cost-effective prevention or treatment for underserved children most susceptible to LAP.

We used a sensitive cytokine assay that analyzed 21 cytokines in saliva in a longitudinal study of periodontal disease. Periodontal disease is a progressive disease that results in bone loss over time. In our studies we took saliva samples every 6 months and found that of the group that developed bone loss only one cytokine was elevated 6 months prior to bone loss. That cytokine was MIP 1a and an extensive review of the literature indicated that MIP 1a was also elevated many months prior to active bone loss in multiple myeloma, a sever cancer that results in massive bone loss throughout the body. Our data and the literature reviewed suggested that MIP 1a is a cytokine that both; 1) attracts monocytes to areas of bone resorption, and 2) then signals these monocytes to become active osteoclasts that cause bone resorption. In our study we were surprised to find that we could detect elevated levels of MIP 1a in the saliva of patients any where from 6-9 months prior to x-ray evidence of bone loss in these same patients. In addition we have been able to detect both RANKL and Osteoprotegerin in saliva.

Follow-Up

One question that has been raised is whether saliva can show enough of a concentrated level of the marker to make a determination. In periodontal disease the markers come from the pocket overlying the infected tooth and then these proteins spill over into saliva. The question is whether at the time these proteins are seen in saliva, there presence is at a high enough concentration for detection in saliva. Put differently is there such a dilution factor in saliva that these proteins are present in saliva at too low a level for detection? In efforts to answer this question we have done a pilot study in which we studied the presence of RANKL in saliva and compared it to that seen in crevicular fluid in pockets surrounding teeth that were either healthy or periodontally diseased. We measured these elements in gingival crevicular fluid in healthy sites in some patients and in pockets in diseased patients and found the presence of these markers in saliva at a detectable level even in cases where only one pocket existed. These results suggest that saliva is capable of detecting these elements from just one pocket site.

Further we have also done a small study that examined individuals who were undergoing tooth movement where bone loss is generated by force as opposed to infection (as in the case of periodontal disease). In this case both saliva and crevicular fluid was collected and assayed for the presence and level of the markers seen in periodontal disease. Whereas in the case of periodontal bone loss a 40 fold elevation in the biomarker MIP 1 alpha was seen in the diseased subjects, in this case no difference was seen in patients undergoing severe tooth movement as compared to controls with respect to levels of MIP 1 alpha. These findings suggest that MIP 1 alpha as biomarker of bone loss in the case of periodontal disease will not be confused with bone loss resulting from physical trauma (i.e. tooth movement). Thus traumatic bone loss measures will not conflict with bone loss resulting from inflammatory response to infection. These findings suggest that the mechanisms for bone loss are different and this is reflected in the bone markers seen in the crevicular fluid and in the saliva. Thus use of MIP 1 alpha as a salivary test to predict radiographic evidence of bone loss in periodontal disease will not be confused with bone loss resulting from orthodontic tooth movement or other traumatic stressors.

Example 2

Osteoporosis

We gathered the stored saliva of the 6 bone loss subjects and the saliva from 6 infection positive students who remained healthy as well as saliva from 6 infection negative students who remained healthy, from the periodontal study described above. Thus we had 18 saliva samples, 6 from each of three groups; the infection-positive group with bone loss, the infection-positive group without bone loss and the infection-negative group without bone loss. 100 ul of clarified whole saliva was obtained from the patient the visit before bone loss was detected (within 9 months prior) and then submitted for evaluation using an assay that determined the levels of 21 cytokines and chemokines. For this salivary evaluation we used the xMAP technology that utilizes 5.6 micron polystyrene microspheres that are internally labeled with red and infrared fluorophores. Multiplexed signals are detected from 100 distinct sets of color coded beads. Each bead set is coated with a reagent that is excited to a distinct detectable level in a particular bioassay. In this case all cytokines are treated exactly the same and thus the internal controls are outstanding.

Results from the assay were as follows: Il 2, 3, 4, 5, RANTEs and TNFa were not detected. GM-CSF, IFNg, Il, 1a, Il 8, 10, 12, 13 and 15 were found but no difference were seen when groups were compared. A trend was found that suggested that for IL 1b was elevated in the infection positive group but this was not statistically significant. However, MIP 1a was statistically significantly elevated in the infection-positive group that had bone loss vs. those in the infection positive or in the infection-negative groups who remained healthy and thus did not have bone loss. The p value for this comparison was equal to p=0.001 suggesting that this cytokine could be useful in distinguishing between those that have developed bone loss and those who did not. Since this chemokine has been shown to precede bone loss in multiple myeloma and in bone loss derived from a similar in vitro infection of periodontal disease, we are greatly encouraged that this finding is pertinent particularly since none of the other 20 cytokine indicators were seen to change and thus did not correlate with clinical conditions

We claim:

1. A method of detecting and treating early-stage periodontal bone loss in a patient comprising: collecting a sample of saliva from a patient; measuring the level of MIP 1α in the sample; determining whether the level of MIP 1α present in the sample is indicative of early stage periodontal bone loss; and treating the patient for early-stage periodontal bone loss.

2. The method of claim 1 wherein a level of MIP 1α greater than about 200 pg/ml is indicative of early stage periodontal bone loss.

3. The method of claim 1 wherein a level of MIP 1α from about 200 pg/ml to about 2000 pg/ml is indicative of early stage periodontal bone loss.

4. The method of claim 1 wherein a level of MIP 1α from about 500 pg/ml to about 1,500 pg/ml is indicative of early stage periodontal bone loss.

5. The method of claim 1 wherein a level of MIP 1α from about 750 pg/ml to about 1,250 pg/ml is indicative of early stage periodontal bone loss.

6. The method of claim 1, wherein the MIP 1α is identified prior to radiographic evidence of bone loss.

7. A method of detecting and treating increased periodontal pocket depth in a patient comprising: collecting a sample of saliva from a patient; measuring the level of MIP 1α in the sample; determining whether the level of MIP 1α present in the sample is indicative of increased periodontal pocket depth; and treating the patient for increased periodontal pocket depth.

8. A method of detecting and treating osteoporosis in a patient comprising: collecting a sample of saliva from a patient; measuring the level of MIP 1α in the sample; determining whether the level of MIP 1α present in the sample is indicative of osteoporosis; and treating the patient for osteoporosis.

9. The method of claim 8 wherein a level of MIP 1α greater than about 200 pg/ml is indicative of osteoporosis.

10. The method of claim 8 wherein a level of MIP 1α greater than about 400 pg/ml is indicative of osteoporosis.

11. The method of claim 8 wherein a level of MIP 1α greater than about 600 pg/ml is indicative of osteoporosis.

12. The method of claim 8 wherein a level of MIP 1α greater than about 800 pg/ml is indicative of osteoporosis.

13. The method of claim 8 wherein a level of MIP 1α from about 200 pg/ml to about 2000 pg/ml is indicative of osteoporosis.

14. The method of claim 8 wherein a level of MIP 1α from about 500 pg/ml to about 1,500 pg/ml is indicative of osteoporosis.

15. The method of claim 8 wherein a level of MIP 1α greater from about 750 pg/ml to about 1,250 pg/ml is indicative of osteoporosis.

16. The method of claim 8, wherein the MIP 1α biomarker is identified prior to radiographic evidence of bone loss.

* * * * *